US012564513B2

(12) United States Patent
Al Sabti

(10) Patent No.: US 12,564,513 B2
(45) Date of Patent: Mar. 3, 2026

(54) TOOL FOR MACULAR ELEVATION

(71) Applicant: Khalid Al Sabti, Kuwait City (KW)

(72) Inventor: Khalid Al Sabti, Kuwait City (KW)

( * ) Notice: Subject to any disclaimer, the term of this patent is extended or adjusted under 35 U.S.C. 154(b) by 0 days.

(21) Appl. No.: 19/239,617

(22) Filed: Jun. 16, 2025

(65) Prior Publication Data

US 2025/0381068 A1     Dec. 18, 2025

Related U.S. Application Data

(60) Provisional application No. 63/660,197, filed on Jun. 14, 2024.

(51) Int. Cl.
*A61F 9/007*          (2006.01)
(52) U.S. Cl.
CPC .................................... *A61F 9/007* (2013.01)
(58) Field of Classification Search
CPC .. A61F 9/007; A61F 9/00736; A61B 17/3421; A61B 17/3496; A61B 17/3201; A61B 17/0231
See application file for complete search history.

(56) References Cited

U.S. PATENT DOCUMENTS

| | | | |
|---|---|---|---|
| 7,326,236 B2 * | 2/2008 | Andreas ................. | A61F 2/966 |
| | | | 623/1.11 |
| 2017/0157336 A1 * | 6/2017 | Olson ................. | A61M 5/3286 |
| 2018/0042768 A1 * | 2/2018 | Charles ............... | A61F 9/00727 |
| 2019/0269555 A1 * | 9/2019 | Cady ................... | A61F 9/00736 |
| 2020/0375844 A1 * | 12/2020 | Maschio ................. | A61F 9/007 |
| 2023/0240888 A1 * | 8/2023 | Hallen ................... | A61F 9/007 |

FOREIGN PATENT DOCUMENTS

DE          102010060900 A1 *  5/2012  ............. A61F 9/007

* cited by examiner

*Primary Examiner* — Andrew Restaino
(74) *Attorney, Agent, or Firm* — Winthrop & Weinstine, P.A.

(57)          ABSTRACT

The present disclosure relates to a novel and advantageous tool for manipulation of the eye. Particularly, the present disclosure relates to a novel and advantageous tool for macular elevation to facilitate surgical reach of the macula for treatment of a macular hole. The tool may have a handle portion and an engagement portion. The engagement portion may have an engagement surface for engaging a rear surface of the eye. The tool may further have an extender for adjusting an extension of the engagement surface from the handle portion.

20 Claims, 10 Drawing Sheets

Single focal point

Focal point in
front of retina

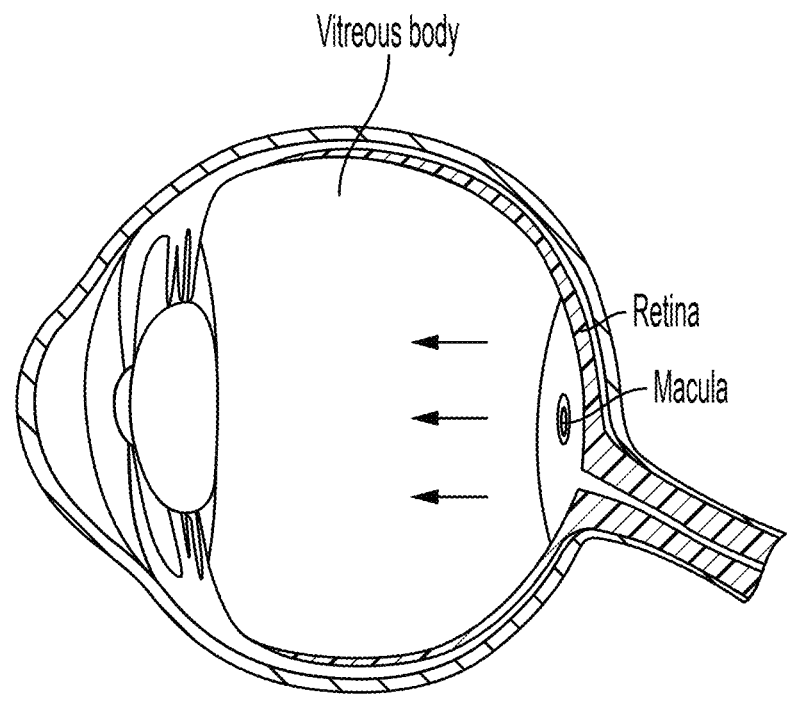
Figure 3a
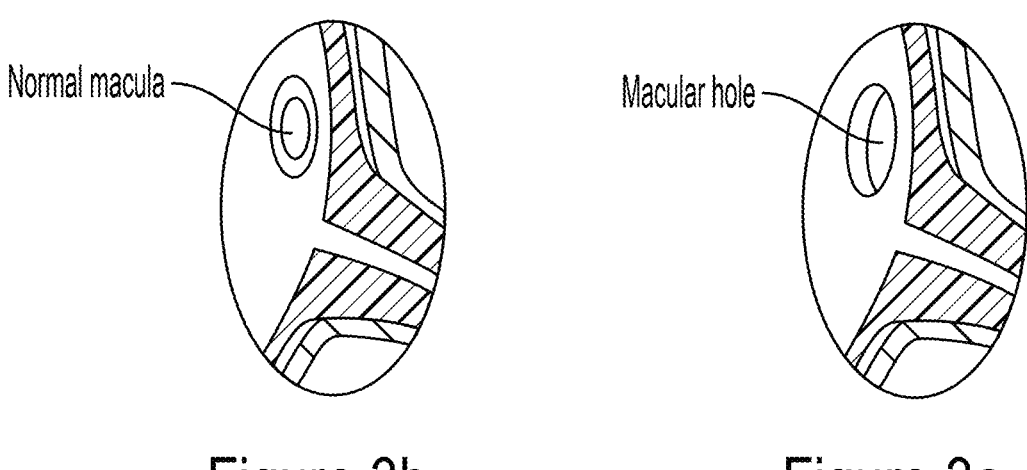
Figure 3b          ## Figure 3c

TOOL FOR MACULAR ELEVATION

CROSS-REFERENCE TO RELATED APPLICATIONS

The present disclosure claims priority to Provisional Application No. 63/660,197, entitled TOOL FOR MACULAR ELEVATION, and filed 14 Jun. 2024, the contents of which are hereby incorporated by reference herein in their entireties.

FIELD OF THE INVENTION

The present disclosure relates to a novel and advantageous tool for manipulation of the eye. Particularly, the present disclosure relates to a novel and advantageous tool for macular elevation. More particularly, the present disclosure relates to a novel and advantageous tool for macular elevation to facilitate surgical reach of the macula for treatment of a macular hole.

BACKGROUND OF THE INVENTION

The background description provided herein is for the purpose of generally presenting the context of the disclosure. Work of the presently named inventors, to the extent it is described in this background section, as well as aspects of the description that may not otherwise qualify as prior art at the time of filing, are neither expressly nor impliedly admitted as prior art against the present disclosure.

FIG. 1 illustrates the anatomy of an eye. As shown, the eye includes a plurality of structures. For purposes of the present disclosure, discussion will be limited primarily to the lens, retina, and macula. The retina is a layer of tissue, including photoreceptor cells and nerve cells, at the back of the eye and functions to convert light into electrical signals that the brain can interpret as vision. It receives focused light from the lens, converts it into nerve signals, and transmits these signals via the optic nerve to the visual cortex for processing. The macula is the central part of the retina and contains a high concentration of photoreceptor cells for light and color detection. The macula is responsible for central vision. The macula is about 5 mm in diameter and has a high concentration of photoreceptor cells, which are important to color vision and sharp vision.

Nearsightedness, also referred to as myopia, is a common vision condition in which close objects look clear but far objects look blurry. Myopia happens when the shape of the eye, or the shape of certain parts of the eye, such as the eyeball being too long or the cornea being too curved, causes light to focus in front of the retina instead of directly on it. When the eyeball is too long from front to back, it can cause light rays to not focus correctly on the retina. When the cornea is too curved, it can cause light rays to end incorrectly. The incidence of myopia has increased significantly in recent years. This may be due to low outdoor time, near work, dim light exposure, and the like.

FIG. 2*a* illustrates an eye with normal vision and its focal point at the retina. FIG. 2*b* illustrates an eye with myopic vision with its focal point in front of the retina. This is due to the eye having a long axial length (AXL). As shown, light rays that should be focused on the retina are instead focused in front of the retina.

The macula is the small area in the center of the retina where light is focused. The macula's function uses its high concentration of photoreceptor cells to process color and detail. A macular hole is a tear or break in the macula. A macular hole can affect central vision, causing blurred, distorted, or wavey vision, and potentially a dark spot in the center of vision. More specifically, macular holes happen when a circular opening forms in the macula, often after being stretched or pulled. As the macular hole forms, objects in a person's central vision look blurry, wavy, or distorted. As the macular hole grows, a dark or blind spot appears in the central vision.

Macular holes are often associated with the natural aging process, where the vitreous gel/body/humor (a jelly-like substance in the eye) detaches from the retina, pulling on the macula and causing a break. FIG. 3*a* illustrates the eye, showing the macula, retina, and vitreous body. FIG. 3*b* illustrates a normal macula. FIG. 3*c* illustrates a macular hole. Macular holes can also be caused by eye disorders like high myopia (nearsightedness), macular pucker, retinal detachment, or injuries to the eye.

A vitrectomy may be performed to treat macular hole. During a vitrectomy, a doctor removes the vitreous body. The surgeon may further perform repairs on the retina. The doctor then replaces the vitreous body with a gas bubble, sterile salt water, or silicone oil. This helps the eye keep its shape and the retina stay in position. The inserted bubble/water/oil acts as a temporary bandage that holds the edges of the macular hole together and helps the eye close the hole. A vitrectomy may be used to treat a variety of conditions beyond macular holes-such as retinal detachment, posterior vitreous detachment, diabetes-related retinopathy, macular pucker, eye injury, endophthalmitis, tumors, lens issues, etc.

A membrane peel is a surgical procedure to remove scar tissue from the macula of the eye. This tissue, which forms on the inner surface of the retina, can cause blurred and distorted vision. The procedure is often performed in conjunction with vitrectomy. An epiretinal membrane peel is a surgical procedure to remove the epiretinal membrane (ERM), a thin layer of scar tissue that can develop on the retina's surface. In some instances, the membrane peel can remove both the ERM and the underlying internal limiting membrane (ILM).

Internal limiting membrane surgery (ILM surgery) is a common procedure used to treat macular holes. It involves removing the internal limiting membrane to create space for the hole to close.

Anatomic success of macular hole closure after surgery can depend on the axial length of the eye. In general, eyes having an axial length of 26 mm to 30 mm has a success rate of 91.7% whereas myopic eyes with an axial length of 30 mm or more have a success rate of 0%.

A membrane peel is typically done using a surgical instrument called ILM forceps. Using the ILM forceps, a surgeon grasps and removes the membrane. During surgery a chandelier light is typically used to free the surgeon's other hand. The conjunctiva and tenons of the surface tissue of the eye are cut at the limbus to allow the instrument to slide freely to reach to the macular region externally through posterior sclera. The success of surgery in such cases of macular hole depends on how successful this surgical maneuver, which is a very delicate step, is performed.

Depending on which eye is being operated on and which hand of the surgeon is dominant, the maximum axial length in which this surgical maneuver is performed varies from 30 mm to 32 mm. Relative shortening of the instrument shaft of the ILM forceps leads to a variety of difficulties in reaching out to the macula. To date there have been few options for addressing difficulties in reaching the macula, whether due to relative shortening of the instrument shaft or eyes having high axial lengths, for example due to myopia.

For membrane peel surgery, a trocar cannula is placed in the wall of the eye to allow instrument introduction and exchanging. One option for addressing difficulties in reaching the macula is to remove the trocar cannula, which provides the surgeon with an extra 1 to 2 mm length to use. Although this might help in a few cases, it typically does not provide sufficient length for eyes having a high axial length.

Another option is to use a specially made extra-long shaft ILM forceps (5 mm longer) which can be used alone or in conjunction with trocar removal. The extra-long shaft ILM forceps are helpful in some cases but are not always available in all operating rooms. In addition, some surgeons are unfamiliar with this instrument. It has been shown that surgeons using unfamiliar forceps can cause damage to the macula more often than if using the forceps that they are very comfortable using.

Another suggested option is using anterior segment ocular coherence tomography (OCT) to identify the beginning of the retina to avoid retina perforation as the instruments are introduced more posterior than the conventional way. Kadanosono et al. *Retina* 43 (5): p 733-738, May 2023. By so doing, the distance from the trocar to the macula is shortened, gaining approximately 2 mm. Using this approach, researchers reported that the maximum axial length at which they could safely operate was 32 mm.

Thus, there is a need in the art for addressing reaching the macula for certain eye surgeries.

BRIEF SUMMARY OF THE INVENTION

The following presents a simplified summary of one or more embodiments of the present disclosure in order to provide a basic understanding of such embodiments. This summary is not an extensive overview of all contemplated embodiments, and is intended to neither identify key or critical elements of all embodiments, nor delineate the scope of any or all embodiments.

The present disclosure, in one or more embodiments, relates to a tool for elevating a macula of an eye comprising a handle portion, an engagement portion, and an extender. The engagement portion is operably coupled to the handle portion and has an engaging surface for engaging a rear surface of the eye. The extender operates to adjust an extension of the engagement surface from the handle portion. The tool functions to pull a rear surface of the eye proximally using the engaging surface and decrease an axial length of the eye during a surgical procedure.

The present disclosure, in one or more embodiments, additionally relates to a tool for elevating a macula of an eye comprising a handle portion, an engagement portion, and an extender. The engagement portion extends from the handle portion and forms a distally moving. The engagement portion includes a shaft and a distal curved engaging surface, the distal cured engaging surface being configured to engage a rear surface of the eye. A proximal end of the shaft is received by a distal end of the handle portion. The extender is configured to extend the engagement portion distally.

While multiple embodiments are disclosed, still other embodiments of the present disclosure will become apparent to those skilled in the art from the following detailed description, which shows and describes illustrative embodiments of the invention. As will be realized, the various embodiments of the present disclosure are capable of modifications in various obvious aspects, all without departing from the spirit and scope of the present disclosure. Accordingly, the drawings and detailed description are to be regarded as illustrative in nature and not restrictive.

BRIEF DESCRIPTION OF THE DRAWINGS

While the specification concludes with claims particularly pointing out and distinctly claiming the subject matter that is regarded as forming the various embodiments of the present disclosure, it is believed that the invention will be better understood from the following description taken in conjunction with the accompanying Figures, in which:

FIG. 3a illustrates the eye, showing the macula, retina, and vitreous body.
FIG. 3b illustrates a normal macula.
FIG. 3c illustrates a macular hole.
FIG. 7b illustrates an enlarged view of a portion of the tool as shown in FIG. 7a.
FIG. 8b illustrates an enlarged view of a portion of the tool as shown in FIG. 7a.

DETAILED DESCRIPTION

The present disclosure relates to a novel and advantageous tool for manipulation of the eye. Particularly, the present disclosure relates to a novel and advantageous tool for macular elevation. More particularly, the present disclosure relates to a novel and advantageous tool for macular elevation to facilitate surgical reach of the macula in surgeries such as treatment of a macular hole.

The disclosed tool, also referred to as a macular elevator, may be used in surgical situations where there is a need to improve the reachability of the macula. The macular elevator elevates the macula, thereby reducing length of the eye during surgery. In most surgical treatment of macular hole, surgery can be performed with conventional use of surgical instruments. Current surgical instruments have a standard shaft length suitable for most retina cases. Human eye length, referred to as axial length, varies from 16 mm to 38 mm or more. As the axial length of an eye increases, as in high myopia, so does the difficulty in performing surgery on the eye, at least because typical instruments do not allow engagement of the macula at an axial length of 32 mm or more. Particularly in cases of myopic macular hole, such axial length can make achieving engagement with the macula difficult.

Figure 1:
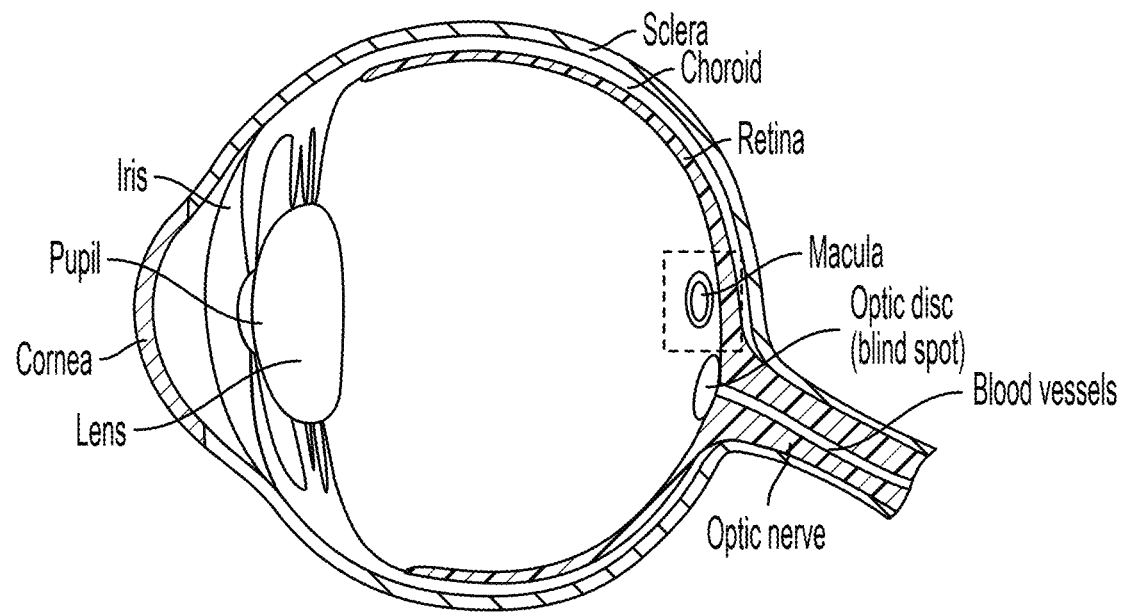
FIG. 1 illustrates the anatomy of an eye.
Figure 2A:
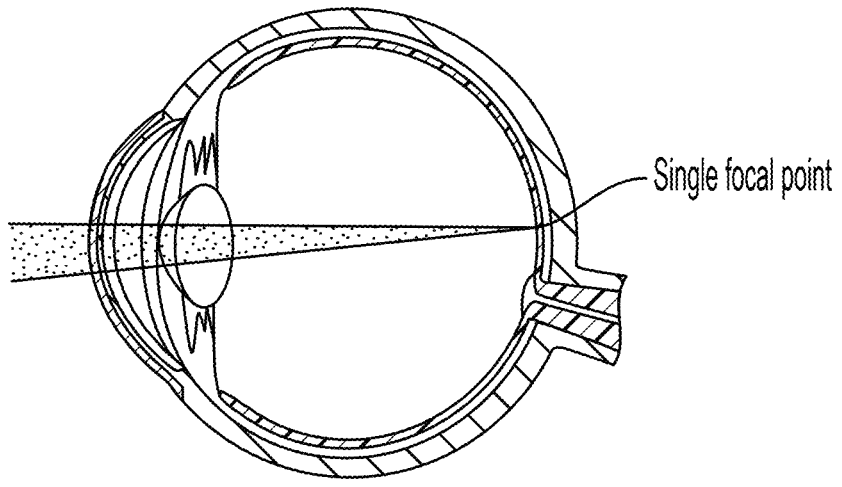
FIG. 2a illustrates an eye with normal vision.
Figure 2B:
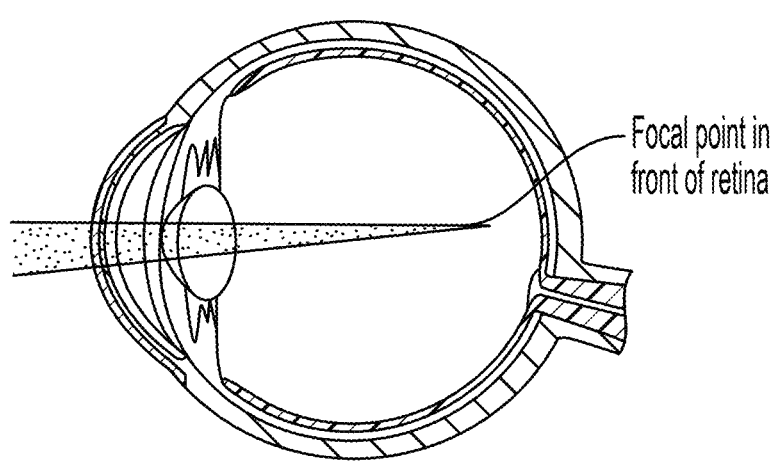
FIG. 2b illustrates an eye with myopic vision.
Figure 4A:
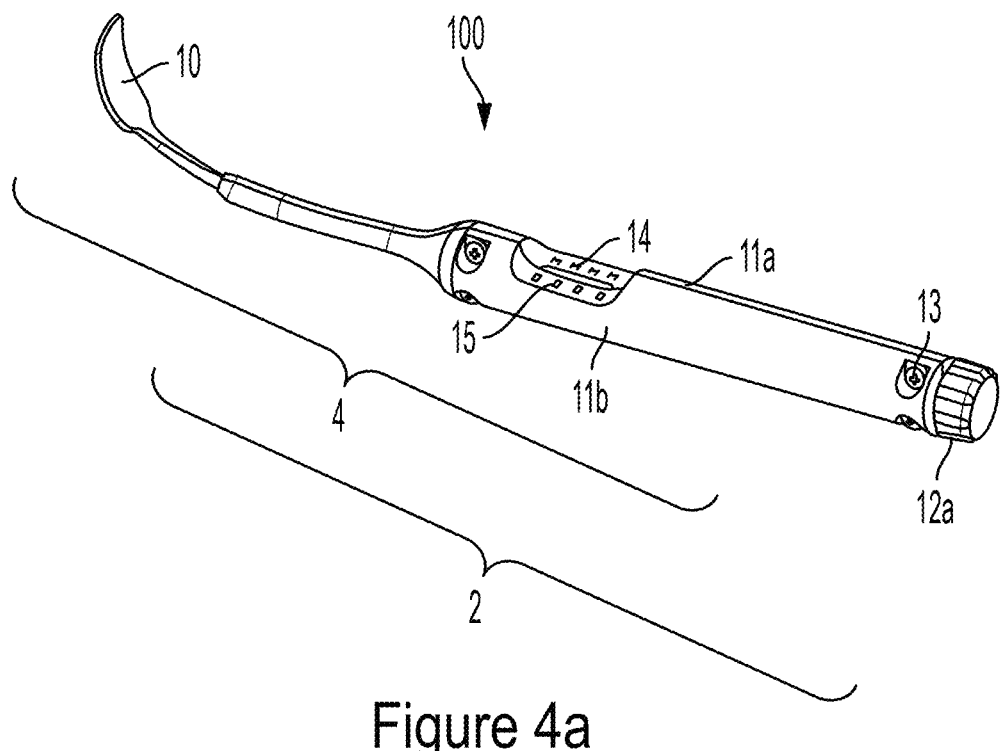
FIG. 4a illustrates a perspective view of a tool for macular elevation, in accordance with one embodiment.
Figure 4B:
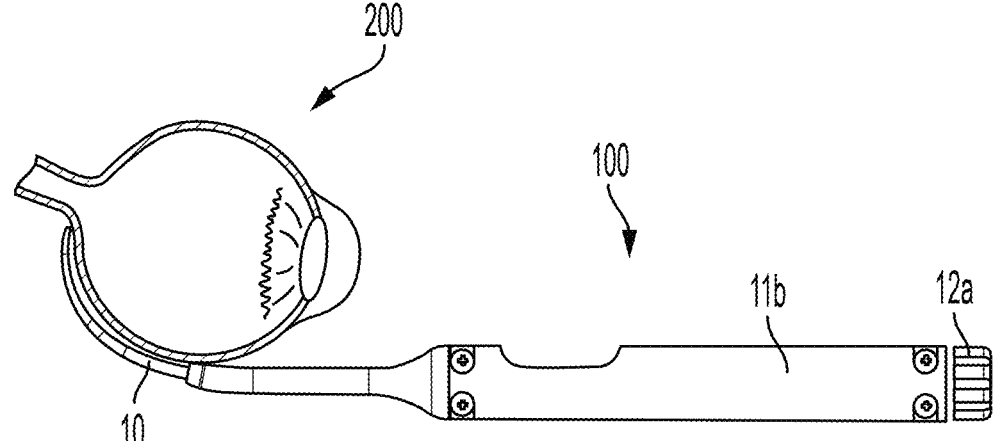
FIG. 4b illustrates a side view of the tool of FIG. 4a with an engagement surface inserted behind the eye but not yet engaging the eye, in accordance with one embodiment.

FIG. 4a illustrates a perspective view of a macular elevation tool 100, referred to as a macular elevator, in accordance with one embodiment. The macular elevator can be used in surgical procedures on eyes having high axial lengths. A specific use for the macular elevator is treatment of a macular hole of a myopic eye by way of ILM surgery. In such surgery, surgical instruments such as ILM forceps are may be short of reaching out to the macula to safely perform the surgery. The macular elevator may be used to decrease the axial length of the eye during surgery such that the ILM forceps, or other surgical too, can reach the macula. FIG. 4b illustrates a side view of the tool of FIG. 4a with the engagement surface 10 inserted behind the eye 200 but not yet engaging the eye 200.

The macular elevator 100 may be handheld instrument having a handle portion 2 and an engagement portion 4. The macular elevator 100, or at least the engagement portion 4 of the macular elevator, may comprise a surgical grade material such as stainless steel, titanium, a polymer (such as PEEK), ceramic, tungsten carbide, and the like. The handle portion 2 is configured for engagement by a surgeon's hand. The engagement portion 4 has a shaft and a curved end forming an engaging surface 10. In some embodiments, the engaging surface is a curved planar surface. The handle portion and the engagement portion are operably connected. An extender, such a push-pull mechanism, may be provided to facilitate adjustment of extension of the engagement surface away from the handle portion such that the macular elevator can be used more precisely with different lengths of the eye. While a specific type of extender is described, it is to be appreciated that any mechanism for extending and retracting the engagement surface may be used. In some embodiments, the macular elevator can accommodate axial lengths ranging from, for example, 32 mm to 38 mm. The extension of the engagement surface can be adjusted by a user. In some embodiments, the extension of the engagement surface from the handle portion may be fixed.

The handle portion 2 includes handle 11a, 11b, indicators 14, 15, and an extender 12a, 12b. In the embodiment shown, the extender 12a is a rotating knob. The engaging surface 10 forms a distally moving depressor, the extension of which may be controlled by the extender 12a. More specifically, the extender 12a may be used to extend and retract the engagement surface. The selected extension of the engagement surface may be shown at indicators 14, 15. Screws 13, or other fixation elements, may be used to couple handle parts 11a and 11b. In the embodiment shown, the handle comprise two parts 11a and 11b. The two parts are coupled together such as by screws 13 or other fixation elements, snap fit, or an adhesive. In other embodiments, the handle may have a unitary construction.

Figure 5:
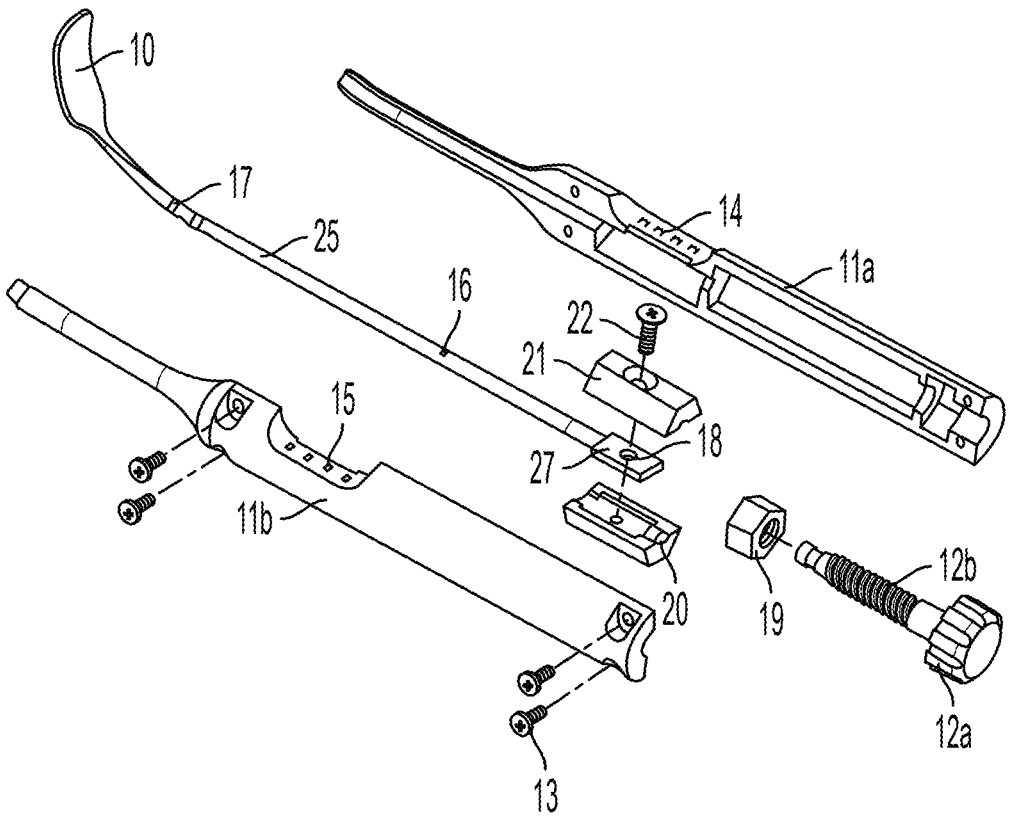
FIG. 5 illustrates an exploded view of the tool of FIG. 4a, in accordance with one embodiment.
Figure 6:
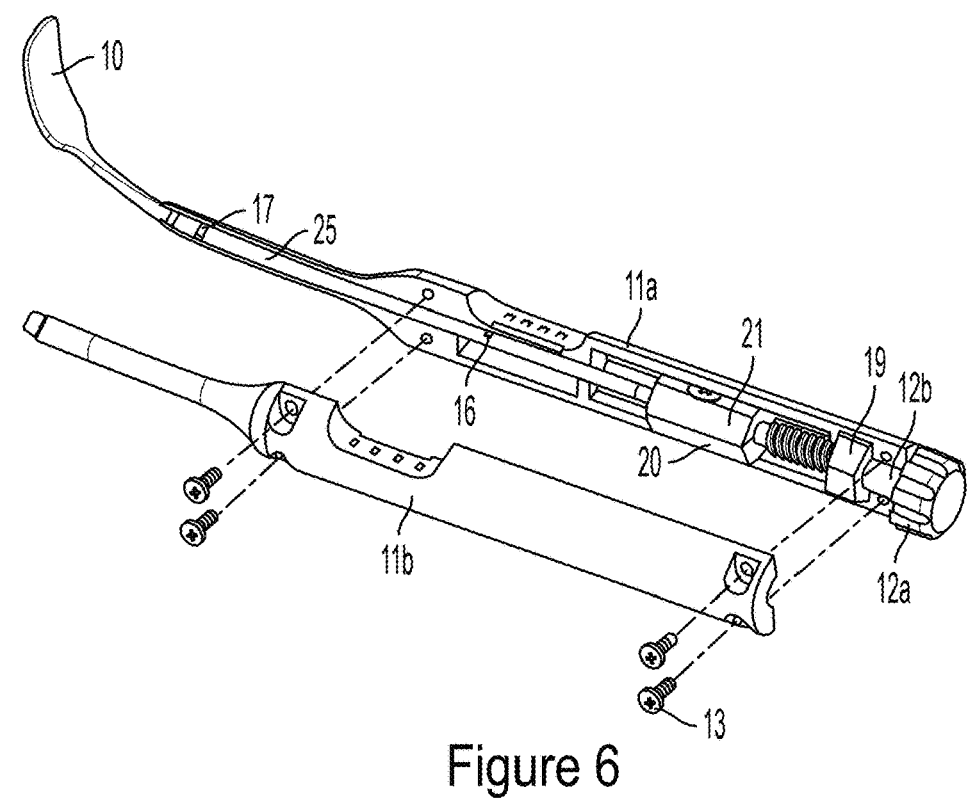
FIG. 6 illustrates a view of the macular elevator of FIG. 4a with handle portions separated, in accordance with one embodiment.
Figure 7A:
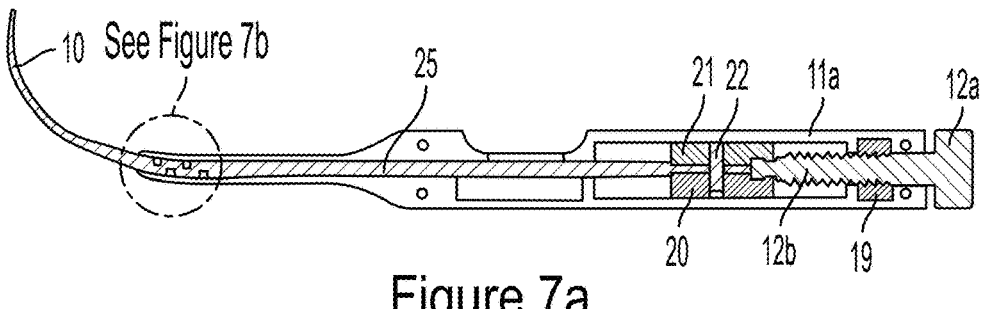
FIG. 7a illustrates a cross-sectional view of the tool of FIG. 4a, in accordance with one embodiment.
Figure 7B:
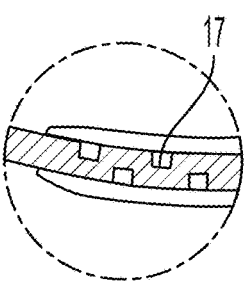

FIG. 5 illustrates an exploded view of the tool of FIG. 4a. FIG. 6 illustrates a view of the macular elevator of FIG. 4a with handle portions 11a and 11b separated. FIG. 7a illustrates a cross-sectional view of the tool of FIG. 4a with detail of the grooves 17. FIG. 7b illustrates an enlarged view of the interface of the engagement portion and the handle.

The engagement portion includes a shaft 25 and an engagement surface 10. The handle 11a, 11b has a proximal end (proximate the user) and a distal end (proximate the patient). The distal end of the handle portion receives the shaft 25 of the engagement portion. The handle may be generally cylindrical and taper towards a distal end thereof to facilitate receipt of the shaft 25.

An extender 12a, 12b is provided at the proximate end of the handle. In the embodiment shown, the extender comprises a rotating knob 12a and a pusher 12b, the pusher 12b comprising a threaded shaft. The knob 12a may be used to adjust distal extension of the engaging surface 10 of the engagement portion by pressing the pusher 12b against the shaft 25 of the engagement portion. It is to be appreciated an alternative extenders may be used, the extender may be provided at a different location on the tool, and/or different methods of adjusting the extension of the engagement surface may be used.

The handle 11a, 11b houses a length of the shaft 25 engagement portion. A proximal portion 27 of the shaft is encased in a housing 20, 21. The proximal portion 27 may comprise for example, a tab to facilitate encasement by the housing 20, 21. At the proximal end of the handle, a connecting element to the pusher 12b is provided that allows back and forth movement (extension and retraction) of the engaging surface 10 to a desired length.

The housing may comprise two parts 20 and 21. The two parts 20, 21 of the housing may be connected in any suitable manner, such as using fixation elements, an adhesive, or a snap fit. In the embodiment shown, the two parts 20, 21 are connected with a screw 22 through a hole 18 in the tab 27 of the shaft 25.

A threaded bolt 19 is provided in the handle 11a, 11b proximal of the housing 20, 21. The pusher screw 12b extends from the knob 12a and through the threaded bolt 19 into the housing 20, 21. The pusher screw 19 engages the proximal end 27 of the shaft 25 of the engagement portion (seen best in FIG. 7a). Rotation of the knob 12a causes axial movement of the pusher screw 12b, which in turn causes axial movement of the shaft 25 of the engagement portion.

The engagement portion has an indicator marking 16 that indicates the distance of extension of the engaging surface 10 to be referenced at the handle indicator 14, 15. The engagement portion may further include one or more grooves 17 near the transition of the engagement portion from the shaft to the engaging surface 10. The grooves 17 facilitate bending of the shaft for smooth movements.

Figure 8A:
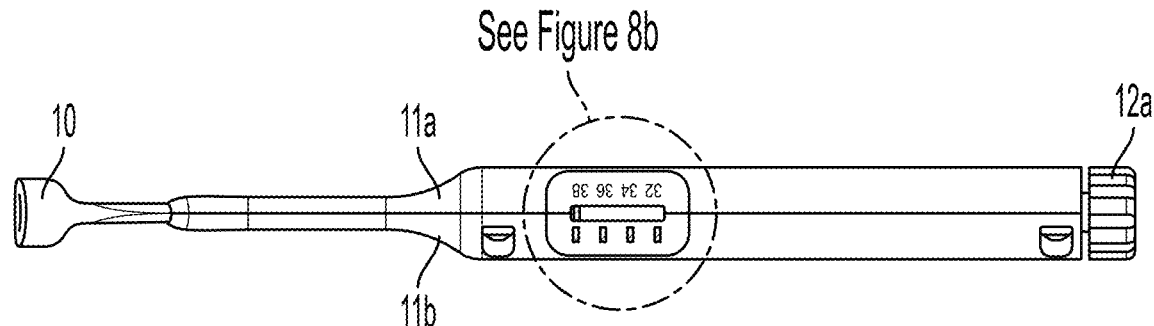
FIG. 8a illustrates a top view of the tool of FIG. 4a, in accordance with one embodiment.
Figure 8B:
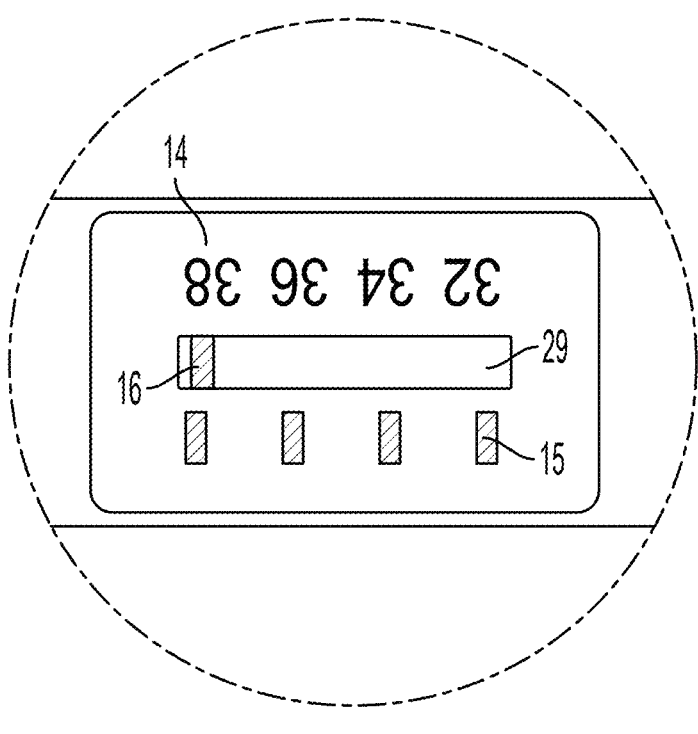

An indicator may be provided for illustrating the extension of the engagement surface 10 away from the handle portion. In the embodiment shown, the indicator comprises an indicator marking 16, an indicator window 29 (see FIGS. 8a and 8b), alignment indicators 15, and value indicators 14. The indicator window 29 may be formed via notches on the handle parts 11a and 11b. The alignment indicators 15 and value indicators 14 may be provided on the handle portion. The indicator marking 16 may be provided on the shaft 25 of the engagement portion. The indicator marking 16 is visible through the indicator window 29. Alignment of the indicator marking 16 with an alignment indictor 15 shows that the engagement surface 10 is at a set location. The alignment indicator 15 may correspond to a value indicator 14 that indicates the length of extension of the engagement surface 10. For example, the value indicators 14 may be 32, 34, 36, and 38 to accommodate AXL lengths ranging from 32 mm to 38 mm. The indicators 14, 15 may be provided generally central to the handle 11a, 11b and may be engraved. FIG. 8a illustrates a top view of the tool of FIG. 4a. FIG. 8b illustrates an enlarged view of the indicators, including indicator marking 16, alignment indicators 15, and value indicators 14. In some embodiments, only alignment indicators or only value indicators 14 may be provided for reference with the indicator marking 16.

Figure 9A:
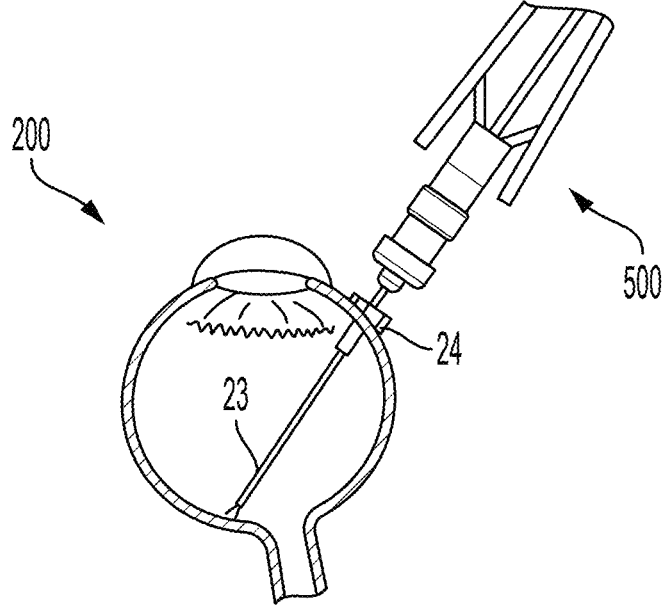
FIG. 9a illustrates an instrument with the tip of the instrument inserted into an eye having a normal AXL.

FIG. 9a illustrates an instrument 500, for example ILM forceps, with the tip 23 of the instrument 500 inserted into an eye 200 having a normal AXL. As shown, a trocar cannula 24 may be used to enter the eye, with ILM forceps 500 inserted therethrough. FIG. 9a illustrates the relationship of ILM forceps 500 to the inner side of the eye and macula in an eye having a normal AXL. Specifically, in an eye having a normal AXL, the tip 23 of the ILM forceps 500 is able to reach the macula at the rear of the eye.

Figure 9B:
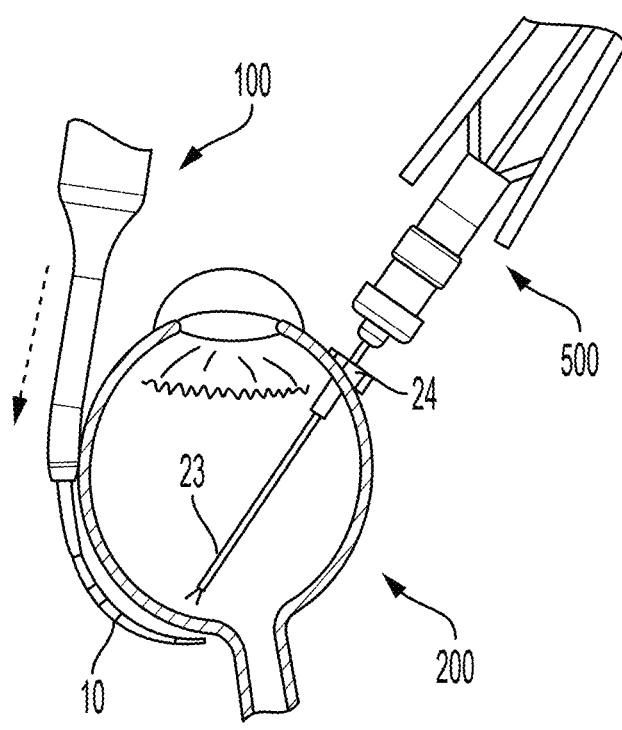
FIG. 9b illustrates an instrument with the tip of the instrument inserted into an eye having a long AXL with a macular elevator positioned for engagement with the eye, in accordance with one embodiment

FIG. 9b illustrates an instrument 500, for example ILM forceps, with the tip 23 of the instrument inserted into an eye 200 having a long AXL with a macular elevator 100 positioned for engagement with the eye but before the engagement surface 10 of the macular elevator 100 is used to elevate the eye 200. FIG. 9b illustrates the short extension of ILM forceps towards the macula in an eye having a long AXL, such as more than 32 mm. As shown, the tip 23 of the instrument is unable to reach the macula at the rear of the eye.

Figure 9C:
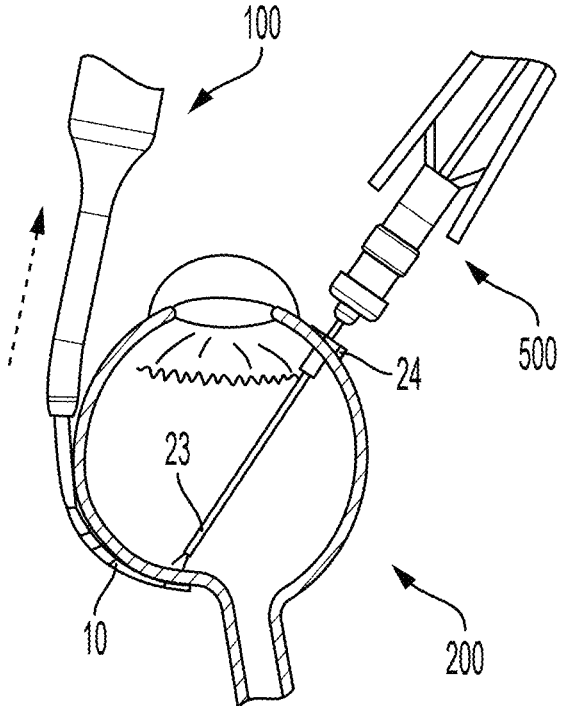
FIG. 9c illustrates an instrument with the tip of the instrument inserted into an eye having a long AXL with the engagement surface of a macular elevator engaging and elevating the eye, in accordance with one embodiment.

FIG. 9c illustrates an instrument 500, for example ILM forceps, with the tip 23 of the instrument inserted into an eye having a long AXL with the engagement surface 10 of a macular elevator 100 engaging and elevating the eye 200. More specifically, FIG. 9c illustrates the relationship of ILM forceps to the inner side of the eye and macula in an eye having a long AXL, such as more than 32 mm, wherein the eye is elevated by the macular elevator 100. As shown, the macular elevator 100 functions to bring the rear of the eye proximally and decrease the AXL during the surgical procedure such that the tip 23 of the instrument 500 is able to reach out to the macula. FIG. 9c illustrates a macular elevator 100 inserted behind the eye with the engagement surface 10 engaging the eye 200. This provides posterior scleral indentation to shorten the eye (by pulling the macular elevator up) and shortening the AXL for the instrument tip 23 to reach out to the macula In use, a user may hold the ILM forceps in one hand and the macular elevator in the other hand. The macular elevator is positioned gently to the macula to initiate a gentle elevation sufficient to perform the surgical maneuver. The location of the engaging surface of the macular elevator is clear because it indents the eye from outside, rendering placement of the tip visible.

It should be appreciated that the tool for macular elevation is described specifically with respect to ILM, it may be used with other types of eye surgery.

As used herein, the terms "substantially" or "generally" refer to the complete or nearly complete extent or degree of an action, characteristic, property, state, structure, item, or result. For example, an object that is "substantially" or "generally" enclosed would mean that the object is either completely enclosed or nearly completely enclosed. The exact allowable degree of deviation from absolute completeness may in some cases depend on the specific context. However, generally speaking, the nearness of completion will be so as to have generally the same overall result as if absolute and total completion were obtained. The use of "substantially" or "generally" is equally applicable when used in a negative connotation to refer to the complete or near complete lack of an action, characteristic, property, state, structure, item, or result. For example, an element, combination, embodiment, or composition that is "substantially free of" or "generally free of" an element may still actually contain such element as long as there is generally no significant effect thereof.

To aid the Patent Office and any readers of any patent issued on this application in interpreting the claims appended hereto, applicants wish to note that they do not intend any of the appended claims or claim elements to invoke 35 U.S.C. § 112(f) unless the words "means for" or "step for" are explicitly used in the particular claim.

Additionally, as used herein, the phrase "at least one of [X] and [Y]," where X and Y are different components that may be included in an embodiment of the present disclosure, means that the embodiment could include component X without component Y, the embodiment could include the component Y without component X, or the embodiment could include both components X and Y. Similarly, when used with respect to three or more components, such as "at least one of [X], [Y], and [Z]," the phrase means that the embodiment could include any one of the three or more components, any combination or sub-combination of any of the components, or all of the components.

In the foregoing description various embodiments of the present disclosure have been presented for the purpose of illustration and description. They are not intended to be exhaustive or to limit the invention to the precise form disclosed. Obvious modifications or variations are possible in light of the above teachings. The various embodiments were chosen and described to provide the best illustration of the principals of the disclosure and their practical application, and to enable one of ordinary skill in the art to utilize the various embodiments with various modifications as are suited to the particular use contemplated. All such modifications and variations are within the scope of the present disclosure as determined by the appended claims when interpreted in accordance with the breadth they are fairly, legally, and equitably entitled.

What is claimed is:

1. A tool for elevating a macula of an eye, the tool comprising:
   a handle portion;
   an engagement portion operably coupled to the handle portion, the engagement portion having an engaging surface configured for engaging a rear, exterior surface of the eye; and
   an extender operable to adjust an extension of the engagement surface from the handle portion in the distal direction;
   wherein the tool is configured to pull the rear surface of the eye proximally using the engaging surface to decrease an axial length of the eye during a surgical procedure.

2. The tool of claim 1, wherein the engaging surface comprises a curved planar surface.

3. The tool of claim 2, wherein the engagement portion further comprises a shaft and the engaging surface is provided at a distal end of the shaft.

4. The tool of claim 3, wherein a proximal end of the shaft is received by a distal end of the handle portion.

5. The tool of claim 1, wherein the extender comprises a knob and a threaded shaft, wherein the knob is operable to turn the threaded shaft, and the threaded shaft is operable to push the engagement portion distally thereby increasing the extension of the engagement surface from the handle portion.

6. The tool of claim 1, wherein the extender comprises a push-pull mechanism.

7. The tool of claim 1, wherein the engagement portion includes an indicator marking for indicating a distance of the extension of the engaging surface.

8. The tool of claim 7, wherein the handle portion includes an indicator window, wherein the indicator marking is visible through the indicator window.

9. The tool of claim 8, wherein the handle portion includes at least one of an alignment indicator and a value indicator.

10. The tool of claim 9, wherein the value indicator provides a numerical indication of the distance of extension of the engaging surface.

11. The tool of claim 1, wherein the engagement portion comprises stainless steel.

12. The tool of claim 1, wherein a distal end of the handle portion is curved.

13. A tool for elevating a macula of an eye, the tool comprising:
   a handle portion;
   an engagement portion extending from the handle portion and forming a distally moving depressor, wherein the engagement portion includes a shaft and a distal curved engaging surface, the distal curved engaging surface being configured to engage a rear, exterior surface of the eye, and wherein a proximal end of the shaft is received by a distal end of the handle portion;
   an extender configured to extend the engagement portion distally relative to the handle portion.

14. The tool of claim 13, wherein the extender is configured to retract the engagement portion proximally.

15. The tool of claim 13, wherein the extender comprises a knob and a threaded shaft, wherein when the knob turns the threaded shaft, and the threaded shaft pushes the engagement portion distally thereby extending the distal curved engaging surface a greater distance from the handle portion.

16. The tool of claim 13, wherein the engagement portion includes an indicator marking for indicating a distance of the extension of the distal curved engaging surface.

17. The tool of claim 16, wherein the handle portion includes an indicator window, wherein the indicator marking is visible through the indicator window.

18. The tool of claim 17, wherein the handle portion includes at least one of an alignment indicator and a value indicator.

19. The tool of claim 18, wherein the value indicator provides a numerical indication of the distance of extension of the engaging surface.

20. A system comprising:
   a tool comprising,
      a handle portion; an engagement portion extending from the handle portion and forming a distally moving depressor, wherein the engagement portion includes a shaft and a distal curved engaging surface, the distal curved engaging surface being configured to engage a rear, exterior surface of the eye, wherein a proximal end of the shaft is received by a distal end of the handle portion; and
      an extender configured to extend the engagement portion distally relative to the handle portion, and
   an ILM forceps.

* * * * *